United States Patent [19]

Smith

[11] E Re. 30,029

[45] Reissued Jun. 12, 1979

[54] ABSORBENT MASS OF ALLOY FIBERS OF REGENERATED CELLULOSE AND POLYACRYLIC ACID SALT OF ALKALI-METALS OR AMMONIUM

[75] Inventor: Frederick R. Smith, Wilmington, Del.

[73] Assignee: Avtex Fibers Inc., Valley Forge, Pa.

[21] Appl. No.: 608,304

[22] Filed: Aug. 27, 1975

Related U.S. Patent Documents

Reissue of:

[64] Patent No.: 3,844,287
Issued: Oct. 29, 1974
Appl. No.: 259,944
Filed: Jun. 5, 1972

[51] Int. Cl.[2] ..... A61F 13/20

[52] U.S. Cl. ..... 128/285; 128/296; 260/17.4 CL; 260/17.4 GC

[58] Field of Search ..... 260/17.4 GC, 17.4 CL; 128/285, 284, 270, 296, 263

[56] References Cited

U.S. PATENT DOCUMENTS

| | | | |
|---|---|---|---|
| 2,993,018 | 7/1961 | Steinlin | 260/17.4 |
| 3,187,747 | 6/1965 | Burgeni et al. | 128/285 |
| 3,628,534 | 12/1971 | Donohue | 128/285 |
| 3,669,103 | 6/1972 | Harper et al. | 128/284 |
| 3,670,731 | 6/1972 | Harmon | 128/284 |
| 3,686,024 | 8/1972 | Nankee et al. | 117/140 |

OTHER PUBLICATIONS

Z. Physik. Chem. A181, 249-282 (1938), Werner Kern.
Annalen der Chemie, vol. 322, pp. 387-390, Wolff.

*Primary Examiner*—Edward M. Woodberry
*Attorney, Agent, or Firm*—Arthur R. Eglington

[57] ABSTRACT

A mass of alloy fibers of polyacrylic acid salt of alkali-metals or ammonium and regenerated cellulose, useful for absorbing fluids, are prepared by mixing a caustic solution of polyacrylic acid with viscose, spinning the mixture into fibers and obtaining dry fibers in the alkaline state. The fibers are advantageously dried with an alkaline lubricating finish thereon and then processed into dressings, sanitary napkins, tampons and diapers.

12 Claims, No Drawings

ABSORBENT MASS OF ALLOY FIBERS OF REGENERATED CELLULOSE AND POLYACRYLIC ACID SALT OF ALKALI-METALS OR AMMONIUM

Matter enclosed in heavy brackets [ ] appears in the original patent but forms no part of this reissue specification; matter printed in italics indicates the additions made by reissue.

Alloy fibers consisting of sodium carboxymethyl cellulose and regenerated cellulose have been used as absorbent fibers in articles designed to absorb body fluids. While these alloy fibers are quite useful for this purpose, they are relatively expensive. The carboxymethyl cellulose-regenerated cellulose fiber is difficult to dry down to cardable form from an aqueous system. These fibers may be readily finished and dried by solvent exchange but this adds considerably to the cost of manufacturing the fibers.

It is an object of this invention to provide a highly fluid absorbent mass of alloy fibers of sodium polyacrylate and regenerated cellulose.

It is another object of this invention to provide a method of preparing absorbent alloy fibers of sodium polyacrylate and regenerated cellulose.

These and other objects are accomplished in accordance with this invention which is an article of manufacture comprising a highly fluid absorbent mass of alloy fibers, said fibers comprising a matrix of regenerated cellulose and sodium polyacrylate uniformly dispersed therein.

The alloy fibers are prepared by mixing an aqueous solution of sodium polyacrylate or aqueous solution of sodium hydroxide and polyacrylic acid with viscose at any stage of ripening, forming the mixture into fibers, coagulating and regenerating the fibers, and driving the fibers in the alkaline state. Advantageously, the fibers are coagulated and regenerated in an acid bath, washed, finished by application of an aqueous alkaline finish composition for cellulose, and dried. These fibers are now alkaline and cardable, and are prepared in a conventional manner into articles for absorbing body fluids, *such as pads.*

Sodium polyacrylate solutions or polyacrylic acid emulsions are readily commercially available and need not be described in detail. The solutions which are mixed with the viscose preferably have solids concentrations of from about 2.5 to about 13 percent. Sodium hydroxide is added to polyacrylic acid emulsions to obtain the sodium polyacrylate solutions.

The filament-forming viscose used herein is also well known and need not be described in detail. In general, alkali cellulose is reacted with carbon disulfide and the resulting sodium cellulose xanthate is diluted with sodium hydroxide to produce the viscose which is aged to spinning viscosity. Additives or modifiers may be mixed with the viscose, if desired.

The alloy fiber which is formed predominantly from viscose is coagulated and regenerated by known means and preferably in an acid bath containing sulfuric acid and sodium sulfate. Zinc sulfate is often incorporated in the bath as well as other coagulation modifiers, as desired.

The sodium polyacrylate solution may be mixed with the viscose at any stage of the viscose ripening. Conventionally, the sodium polyacrylate solution is injected into the viscose stream of a spinning machine by means of a metering pump. The amount of sodium polyacrylate which is incorporated in the viscose ranges from about 5 to about 35 percent based on the weight of the cellulose in the viscose. The cellulose in the viscose will preferably range from about 6 to about 10 percent based on the weight of the viscose solution.

After injection or mixing of the sodium polyacrylate into the viscose, the mixture may be run through a blender or homogenizer to assure a thorough mix, if desired. The mixture is then pumped to the spinneret and extruded in the form of fibers into a coagulating medium. After coagulation and at least partial regeneration, the fibers are stretched, if desired, conventionally wet processed and treated with an aqueous lubricating finish composition. The fibers are then dried to an alkaline, cardable product.

In the preferred method of this invention, the sodium polyacrylate containing viscose during processing into fibers is alternately in the alkaline state, the neutralized state and the alkaline state. During passage of the viscose solution through the acid coagulating and regenerating bath, the sodium polyacrylate is neutralized. In order to obtain fibers containing sodium polyacrylate as required by the invention, the wet gel fibers are made alkaline preferably in the finish bath. An alkaline bath preceding the finish bath may also be used, if desired.

The aqueous alkaline lubricating finish is preferably a bath containing an aqueous solution of sodium carbonate and sorbitan monolaurate, however, other alkaline agents and lubricating agents may be employed as taught in the art for ordinary rayon yarn. Some examples of finishes for cellulose fibers include partial higher fatty acid esters of sorbitan or mannitan and their polyoxyethylene derivatives, sodium oleate and oleic acid. Some examples of alkaline agents for alkalizing the fibers include dibasic ammonium phosphate, dibasic sodium phosphate, tribasic sodium phosphate, sodium tetraborate and the like.

The fiber is usually cut in the form of staple before drying, dried and shipped to the manufacturer of the absorbent articles. The absorbent articles may require carding of the fibers which is accomplished in the usual manner without difficulty.

In tampon application, the fibers are formed into the tampon in accordance with any desired procedure. They may be blended with any other fibers which may or may not serve to enhance the properties of the absorbent articles. Some fibers with which the alloy fibers of this invention may be blended include rayon, cotton, chemically modified rayon or cotton, cellulose acetate, nylon, polyester, acrylic, polyolefin and similar fibers.

The fluid holding capacity of the alloy fibers in this invention was determined in accordance with the following procedure.

Sample staple fibers are carded or well opened, conditioned and two grams placed in a 1 inch diameter die. The fibers in the die are then pressed to 0.127 inches thickness for one minute, removed and placed on a porous plate (e.g., a Buchner funnel) so that the 1 inch diameter foot of a plunger weighing 2.4 pounds rests on the test pellet. (The plunger is held in a vertical position and is free to move vertically). The pellet is then wetted with water which flows into the funnel from the stem which is connected by a flexible tube to a dropping bottle, the flow of water being controlled by the position of the dropping bottle. After two minutes immersion, the water is drained for three minutes, the wet pellet is removed and weighed. The fluid holding capacity of the fibers in cc./g. is one-half the weight of water in the test pellet.

To demonstrate this invention, the following example is set forth.

Example

A sodium polyacrylate solution (12.5 ) percent solids having 10,000 to 20,000 cps. viscosity) was injected through a metering pump into the viscose stream of a spinning machine. The viscose composition was 9.0 percent cellulose, 6.0 percent sodium hydroxide and 32 percent carbon disulfide, based on the weight of the cellulose. The viscose ball fall was 70 and its common salt test was 8.

The mixture was spun through a 720 hole spinneret into an aqueous spinning bath consisting of 7.5 percent by weight of sulfuric acid, 18 percent by weight of sodium sulfate and 3.5 percent by weight of zinc sulfate. The alloy fibers passed through the bath and were washed with water, desulfurized and washed again with water. The wet gel fibers were then passed through an alkaline finish bath consisting of 1 percent by weight of sodium carbonate and 1 percent by weight of sorbitan monolaurate (Span 20). The fibers were cut, dried and carded. The fluid holding capacity was tested for fibers having different amounts of sodium polyacrylate in the alloy fibers in the previously described test procedure. The results are set forth in the following table along with results for other fibers prepared as above except that these alloy fibers were prepared with polyacrylic acid without the formation of the sodium salt in the dried fiber product.

Table

| | | | |
|---|---|---|---|
| Sodium polyacrylate, % B.O.C.* | 0 | 10 | 20 |
| Fluid held, cc./g. | 2.75 | 4.55 | 6.05 |
| Polyacrylic acid, % B.O.C.* | 0 | 10 | 20 |
| Fluid held, cc./g. | 2.50 | 3.25 | 3.85 |

*B.O.C. - Based on the weight of the cellulose in the alloy fiber.

From the above data, it is seen that the absorbent mass of alloy fibers, as disclosed herein, has good fluid holding capacity and the sodium salt is necessary to provide distinctly better fluid holding results.

While this invention has been described in terms of sodium polyacrylate, polyacrylate salts of other alkali-metals such as potassium and lithium, and ammonium are also included and may be successfully used to replace sodium polyacrylate in the example.

Various changes and modifications may be made in practicing the invention without departing from the spirit and scope thereof and, therefore, the invention is not to be limited except as defined in the appended claims.

I claim:

1. An article of manufacture comprising a highly fluid absorbent mass of *dry alkaline* alloy fibers [, said alloy fibers] comprising a matrix of regenerated cellulose and polyacrylic acid salt of alkali-metals [or ammonium uniformly] dispersed therein, *said salt being present in an amount ranging from about 5 to about 35 percent, based on the weight of the cellulose.*

[2. The article of claim 1 wherein the polyacrylic acid salt of alkali-metals or ammonium is present in the regenerated cellulose in an amount ranging from about 5 to about 35 percent, based on the weight of the cellulose.]

3. The article of claim 1 wherein the fibers have a lubricating finish for cellulose thereon.

4. The article of claim 1 in the form of a pad.

5. The article of claim 1 in the form of a tampon.

*6. An article as in claim 3 wherein said lubricating finish comprises a partial higher fatty acid ester of sorbitan or mannitan or of a polyoxyethylene derivative thereof.*

*7. An article as in claim 3 wherein said fibers are carded staple fibers, said article comprising a compressed mass of said staple fibers.*

*8. An article as in claim 6, said salt being such, and present in such proportion, that the "fluid holding capacity" is at least 4.55 cc./g., said fluid holding capacity being measured by taking two grams of said fiber in staple form, carded or well opened, placing said two grams of fiber in a 1 inch diameter die, pressing the fibers in the die to 0.127 inch thickness for one minute, removing the resulting pressed test pellet, placing said pellet on a Buchner funnel with a 1 inch diameter foot of a vertically movable plunger weighing 2.4 pounds resting on said pellet, immersing said so-placed pellet in water for two minutes and then draining the water for three minutes, removing the resulting wet pellet and weighing it to determine the amount of water held thereby.*

*9. An article as in claim 1 produced by a method comprising mixing a polyacrylic acid salt of alkali-metals with a filament-forming viscose whereby the viscose predominates in the mixture, forming the mixture into fibers, coagulating and regenerating the fibers, applying a lubricating finish for cellulose to said fibers, and drying the fibers in an alkaline state with said polyacrylic acid salt in said fiber in the form of a sodium salt, said method including the step of cutting the fibers into staple form before drying, the proportion of said polyacrylic acid salt added to said viscose ranging from about 5 to about 35 percent, based on the weight of the cellulose, said lubricating finish comprising a partial higher fatty acid ester of sorbitan or mannitan or of a polyoxyethylene derivative thereof, said sodium salt in said dried alkaline fibers being such, and present in such proportion, that the "fluid holding capacity" is at least 4.55 cc./g., said fluid holding capacity being measured by taking two grams of said fiber in staple form, carded or well opened, placing said two grams of fiber in a 1 inch diameter die, pressing the fibers in the die to 0.127 inch thickness for one minute, removing the resulting pressed test pellet, placing said pellet on a Buchner funnel with a 1 inch diameter foot of a vertically movable plunger weighing 2.4 pounds resting on said pellet, immersing said so-placed pellet in water for two minutes and then draining the water for three minutes; removing the resulting wet pellet and weighing it to determine the amount of water held thereby.*

*10. An article as in claim 8 in which said salt is a sodium salt.*

*11. A dry alkaline alloy fiber comprising a matrix of regenerated cellulose and polyacrylic acid salt of alkali-metals, said fiber having a lubricating finish for cellulose thereon, said salt being such, and present in such proportion, within the range of about 5 to about 35 percent based on the weight of cellulose, that the "fluid holding capacity" is at least 4.55 cc./g., said fluid holding capacity being measured by taking two grams of said fiber in staple form, carded or well opened, placing said two grams of fiber in a 1 inch diameter die, pressing the fibers in the die to 0.127*

*inch thickness for one minute, removing the resulting pressed test pellet, placing said pellet on a Buchner funnel with a 1 inch diameter foot of a vertically movable plunger weighing 2.4 pounds resting on said pellet, immersing said so-placed pellet in water for two minutes and then draining the water for three minutes, removing the resulting wet pellet and weighing it to determine the amount of water held thereby.*

*12. Fiber as in claim 11, said fiber being in staple form and said alkali metal being sodium and said salt being present in amount of at least 10% based on weight of cellulose.*

*13. Fiber produced by a method comprising mixing a polyacrylic acid salt of alkali-metals with a filament-forming viscose whereby the viscose predominates in the mixture, forming the mixture into fibers, coagulating and regenerating the fibers, applying a lubricating finish for cellulose to said fibers, and drying the fibers in an alkaline state with said polyacrylic acid salt in said fiber in the form of a sodium salt, said method including the step of cutting the fibers into staple form before drying, the proportion of said polyacrylic acid salt added to said viscose ranging from about 5 to about 35 percent, based on the weight of the cellulose, said sodium salt in said dried alkaline fibers being such, and present in such proportion, that the "fluid holding capacity" is at least 4.55 cc./g., said fluid holding capacity being measured by taking two grams of said fiber in staple form, carded or well opened, placing said two grams of fiber in a 1 inch diameter die, pressing the fibers in the die to 0.127 inch thickness for one minute, removing the resulting pressed test pellet, placing said pellet on a Buchner funnel with a 1 inch diameter foot of a vertically movable plunger weighing 2.4 pounds resting on said pellet, immersing said so-placed pellet in water for two minutes and then draining the water for three minutes, removing the resulting wet pellet and weighing it to determine the amount of water held thereby.*

* * * * *